(12) United States Patent
Tinker

(10) Patent No.: US 8,070,455 B2
(45) Date of Patent: Dec. 6, 2011

(54) SCOTCH-YOKE MECHANISM FOR REDUNDANT ACTUATION APPLICATIONS

(75) Inventor: Frank A. Tinker, Tucson, AZ (US)

(73) Assignee: Syngardia Systems, Inc,., Tucson, AZ (US)

(*) Notice: Subject to any disclaimer, the term of this patent is extended or adjusted under 35 U.S.C. 154(b) by 290 days.

(21) Appl. No.: 12/498,991

(22) Filed: Jul. 7, 2009

(65) Prior Publication Data

US 2010/0292787 A1 Nov. 18, 2010

Related U.S. Application Data

(63) Continuation-in-part of application No. 12/454,440, filed on May 18, 2009, now Pat. No. 8,021,422.

(51) Int. Cl.
*F04B 49/00* (2006.01)
*F04B 35/02* (2006.01)
*F01B 9/00* (2006.01)
*F16D 31/02* (2006.01)
*A61M 1/10* (2006.01)

(52) U.S. Cl. ............ 417/16; 417/223; 417/319; 92/140; 60/403; 623/3.1

(58) Field of Classification Search ............... 417/413.1, 417/417, 16, 223, 319; 92/140; 60/403; 74/50; 623/3.1, 3.24, 3.25
See application file for complete search history.

(56) References Cited

U.S. PATENT DOCUMENTS

| | | | | |
|---|---|---|---|---|
| 1,349,283 A | * | 8/1920 | Kollock | 74/50 |
| 4,425,880 A | * | 1/1984 | Rochlus | 123/44 C |
| 4,437,808 A | * | 3/1984 | Londos et al. | 414/664 |
| 4,572,013 A | * | 2/1986 | Kasukave | 74/50 |
| 4,876,909 A | * | 10/1989 | Andrei-Alexandru et al. | 74/411.5 |
| 5,848,566 A | * | 12/1998 | Walsh | 92/128 |
| 6,000,264 A | * | 12/1999 | Chang | 72/132 |
| 6,457,306 B1 | * | 10/2002 | Abel et al. | 60/204 |

* cited by examiner

*Primary Examiner* — Charles Freay
(74) *Attorney, Agent, or Firm* — Antonio R. Durando

(57) ABSTRACT

A primary scotch yoke and a secondary scotch yoke are coupled in opposing arrangement and rigidly attached to a linearly reciprocating element. Each scotch yoke includes a rotary actuator with a cam follower and a yoke attached to the reciprocating element. Each yoke has a cam with an open gap through which the follower may be disengaged from the cam and stopped to an idle position. The follower of the secondary scotch yoke is kept idle in a position similarly disengaged from its cam. A controller detects a failure in the primary scotch yoke, disengages the cam follower of the primary yoke from its cam, and energizes the secondary scotch yoke, thereby causing its cam follower to engage its yoke and continue to provide uninterrupted motion to the reciprocating element, in particular the portable pneumatic pump driving an artificial heart.

6 Claims, 10 Drawing Sheets

SCOTCH-YOKE MECHANISM FOR REDUNDANT ACTUATION APPLICATIONS

RELATED APPLICATIONS

This application is a continuation-in-part application of Ser. No. 12/454,440, filed May 18, 2009, entitled "Actuating Mechanism for Pneumatically-Driven Artificial Heart."

BACKGROUND OF THE INVENTION

1. Field of the Invention

This invention relates to a rotary-to-linear motion conversion device suitable for use where redundant rotary actuation is required. In particular, the invention relates to a device for actuating a pneumatic pump driving an artificial heart.

2. Description of the Prior Art

The heart is the muscle that drives the cardiovascular system in living beings. Acting as a pump, the heart moves blood throughout the body to provide oxygen, nutrients, hormones, and to remove waste products. The blood follows two separate pathways in the human body, the so-called pulmonary and systemic circulatory circuits. In the pulmonary circuit, the heart pumps blood first to the lungs to release carbon dioxide and bind oxygen, and then back to the heart. Thus, oxygenated blood is constantly being supplied to the heart. In the systemic circuit, the longer of the two, the heart pumps oxygenated blood through the rest of the body to supply oxygen and remove carbon dioxide, the byproduct of metabolic functions carried out throughout the body. The heart supplies blood to the two circuits with pulses generated by the orderly muscular contraction of its walls.

In order to keep blood moving through these two separate circulatory circuits, the human heart has four distinct chambers that work in pairs. As illustrated in FIG. 1, the heart 10 includes a right atrium 12, a right ventricle 14, a left atrium 16, and a left ventricle 18. One pair of chambers, the right ventricle and left atrium, is connected directly to the pulmonary circuit. In it, de-oxygenated blood from the body is pumped from the right ventricle 14 to the lungs, where it is oxygenated, and then back to the left atrium 16.

In the systemic circuit, the other pair of chambers pumps the oxygenated blood through body organs, tissues and bones. The blood moves from the left atrium 16, where it flows from the lungs, to the left ventricle 18, which in turn pumps the blood throughout the body and all the way back to the right atrium 12. The blood then moves to the right ventricle 14 where the cycle is repeated. In each circuit, the blood enters the heart through an atrium and leaves the heart through a ventricle.

Thus, the ventricles 14,18 are essentially two separate pumps that work together to move the blood through the two circulatory circuits. Four check valves control the flow of blood within the heart and prevent flow in the wrong direction. A tricuspid valve 20 controls the blood flowing from the right atrium 12 into the right ventricle 14. Similarly, a bicuspid valve 22 controls the blood flowing from the left atrium 16 into the left ventricle 18. Two semilunar valves (pulmonary 24 and aortic 26) control the blood flow leaving the heart toward the pulmonary and systemic circuits, respectively. Thus, in each complete cycle, the blood is pumped by the right ventricle 14 through the pulmonary semilunar valve 24 to the lungs and back to the left atrium 16. The blood then flows through the bicuspid valve 22 to the left ventricle 18, which in turn pumps it through the aortic semilunar valve 26 throughout the body and back to the right atrium 12. Finally, the blood flows back to the right ventricle 14 through the tricuspid valve 20 and the cycle is repeated.

When the heart muscle squeezes each ventricle, it acts as a pump that exerts pressure on the blood, thereby pushing it out of the heart and through the body. The blood pressure, an indicator of heart function, is measured when the heart muscle contracts as well as when it relaxes. The so-called systolic pressure is the maximum pressure exerted by the blood on the arterial walls when the left ventricle of the heart contracts forcing blood through the arteries in the systemic circulatory circuit. The so-called diastolic pressure is the lowest pressure on the blood vessel walls when the left ventricle relaxes and refills with blood. Healthy blood pressure is considered to be about 120 millimeters of mercury systolic and 80 millimeters of mercury diastolic (usually presented as 120/80).

Inasmuch as the function of the circulatory system is to service the biological needs of all body tissues (i.e., to transport nutrients to the tissues, transport waste products away, distribute hormones from one part of the body to another, and, in general, to maintain an appropriate environment for optimal function and survival of tissue cells), the rate at which blood is circulated by the heart is a critical aspect of its function. The heart has a built-in mechanism (the so-called Frank-Starling mechanism) that allows it to pump automatically whatever amount of blood flows into it. Such cardiac output in a healthy human body may vary from about 4 to about 15 liters per minute (LPM), according to the activity being undertaken by the person, at a heart rate that can vary from about 50 to about 180 beats per minute.

Several artificial devices have been developed over the years to supplement or replace the function of a failing heart in patients. These include devices developed by companies as well as research institutions such as the Berlin Heart Institute, the Pennsylvania State University, the University of Utah, the Cleveland Clinic Foundation, the University of Perkinje (in Bruno, Czechoslovakia), the University of Tokyo, the Thoratec Corporation, Abiomed Inc., Novacor, and Symbion Inc. Typically, these artificial devices consist of pumps that aim at duplicating the required pumping functions of the left and right human ventricles. One method of actuation for these pumps has been through the pneumatic action of an external mechanism. See, for example, U.S. Pat. Nos. 4,611,578 and 5,766,207. Periodic pulses of compressed air drive the pumps at the desired pressure and rate of cardiac output. A moderate vacuum may be applied between pulses to allow more rapid refilling of the ventricles with blood flowing from the respective atrium.

One notable artificial heart currently in use as an implant for patients waiting for a heart transplant is the Total Artificial Heart manufactured by SynCardia Systems, Inc., of Tucson, Ariz. Designed to operate much the same way as a human heart, this artificial heart replaces the two active chambers (i.e., the ventricles) of the human heart with corresponding artificial components. As illustrated in FIG. 2, such artificial heart 30 includes two separate chambers or ventricles 32 and 34 that replace the right and left ventricles of the human heart, respectively. Each chamber is equipped with a respective diaphragm (36 and 38 in the right and left chamber, respectively) that has an air contact side and a blood contact side. Each diaphragm is designed as a spherical hemisphere. As shown in FIG. 3, the artificial heart 30 is implanted by connecting the top of the right chamber 32 to the right atrium 12 and the top of the left chamber 34 to the left atrium 16. The bottom of each chamber is provided with an air line (40 and 42 in the right and left chamber, respectively) that is embedded in the patient's body but extends outside for connection to a pneumatic driver.

When driven by a supply of pressurized air from the pneumatic driver, each diaphragm 36,38 discharges blood from the respective chamber 32,34 simulating the function of a ventricle. This phase is referred to in the art as systole or equivalently as the ejection phase. When the pressurized air is removed from the diaphragm, known as diastole or the filling phase, blood can enter the ventricle from the connected atrium. The rate at which blood enters the ventricle depends on the difference between the atrial pressure and the pressure on the air-side of the diaphragm. To increase this filling rate, a slight vacuum of about 10 mm Hg is normally applied to the air-side of the diaphragm during diastole. Artificial valves 44a (tricuspid), 46a (bicuspid) and 44b (pulmonary), 46b (aortic) control the flow from the respective atrium into each artificial ventricle and out to the circulatory systems, respectively.

The pneumatic drivers used to date for driving all artificial hearts have been cumbersome and inadequate for affording patients any degree of independent mobility. They employ compressors, vacuum pumps, and air tanks coupled to electrically actuated valves, all of which amounts to a large and heavy apparatus that can only be transported on wheels and with considerable effort. Therefore, many attempts have been made during the last two decades to produce a portable driver for these devices. However, because of the complexity of the required functionality and the hardware necessary to produce it, pneumatic heart drivers continue to be bulky, require frequent maintenance, and often provide air pulses that do not match the performance of the larger drivers they are meant to replace. Even at the approximate weight of 20 pounds and size of about 0.7 cubic feet achieved so far, pneumatic drivers remain unwieldy and substantially not portable for a patient who is kept alive by an artificial heart.

In essence, a portable driver needs to be reliable, durable, easy to use, and sufficiently simple in design to be affordable. Unfortunately, each of these requirements contributes to the complexity of the design, which in turn has produced devices that are not sufficiently small and light-weight to be manageable in the hands of a patient. Furthermore, it is essential that the pneumatic driver be able to provide the correct pressure balance between the left and right ventricles of the artificial heart to ensure the proper operating pressure to the pulmonary and systemic circuits regardless of the speed of operation. Typically, this requires that the driver be able to operate so as maintain, on average, a right atrial pressure of about 9 mmHg, a mean pulmonary artery pressure of about 35 mmHg, a left atrial pressure of about 10 mmHg, and a mean aortic pressure of about 95 mmHg.

This need to provide different operating pressures to the right and left chambers (ventricles) of the artificial-heart device has not been met heretofore with a simple design suitable for a portable driver. For example, the blood pump described in U.S. Pat. No. 4,611,578 includes a configuration wherein two reciprocating pistons in a common cylinder may be operated alternatively to provide redundancy or independently to actuate two separate pneumatically driven blood pumps. This issue is not addressed in the patent, but it describes a sophisticated control system that arguably could be used to provide the correct operating pressure to each chamber of the artificial heart. However, the complex and multi-component structure of the device necessarily requires a relatively heavy and large apparatus, though described as portable. The commercially available module weighs about 25 pounds and is approximately 0.6 cubic feet in volume.

U.S. Pat. No. 5,766,207 describes another portable pneumatic driver for ventricular assist devices that could also be adapted for an artificial heart. The single pump of the invention could be used to drive both ventricles of an artificial heart, but only at the same pressure and volume rate. Thus, this device, even if modified to meet the other requirements of a portable artificial-heart driver, would not be suitable as an alternative to the stationary modules currently in use.

Copending U.S. application Ser. No. 12/454,440, hereby incorporated by reference, describes a portable driver configured to optimize size, weight, reliability, durability, extended battery life, ease of use, and simplicity of design. The driver consists of a pneumatic pump that provides coordinated and independent periodic actuation pressure to each ventricle of the artificial heart, limiting peak pressures and peak vacuums to provide a safe and efficient cycle of operation, allowing only partial filling of each ventricle of the cardiac device to ensure redundancy of capacity, providing sufficient pneumatic stroke to completely eject the blood from the ventricles at each beat, readily adjusting the rate at which the artificial heart is actuated, and minimizing overall size and weight to enable portability.

In the preferred embodiment, the pneumatic pump 50 comprises two coaxial cylindrical pumping chambers (60 and 62) defined by a common housing 52, each enclosing a disk-shaped piston (54 and 56) incorporating seals 66 to eliminate leakage, as illustrated schematically in FIG. 4. The pistons are connected to one another through a partition 58 by a tube 64, thereby forming a monolithic piston assembly that is driven axially by a common electrical actuator 68 providing reciprocating motion through a rod connected to the top piston. The tube travels through a seal in the partition that separates the two chambers and, by defining the boundary between the pistons, also acts as a bulkhead for the top chamber.

The volume in the bottom chamber is selected as needed to provide the desired pressure in the left ventricle of the artificial heart driven by the pump. According to one aspect of the invention, the diameter of the tube connecting the pistons is selected such that the stroke volume (i.e., the displacement) of the top chamber is reduced with respect to that of the bottom chamber as needed to match the reduced pressure requirements of the right ventricle of the artificial heart. Namely, the maximum pressure achieved at the respective output port (70 and 72) in each chamber should be as needed to fully eject blood from each ventricle of the artificial heart substantially at the operating pressures of the human pulmonary and systemic circulatory circuits. A limit check valve (74 and 76) is preferably used in each chamber to ensure venting of excess pressure during the compression stroke. A limit check valve (78 and 80) is also preferably used in each chamber to limit the vacuum generated during the reverse, aspiration stroke.

FIG. 5 illustrates in sectioned view the actual pneumatic driver that incorporates the concepts of the invention disclosed in Ser. No. 12/454,440. As clearly illustrated by FIGS. 4 and 5, the pneumatic pump is actuated by a reciprocating mechanism that drives the pistons. Many such mechanisms are known in the art that could be used to operate the pump. The device commonly referred to as a scotch yoke is preferred because of its simplicity, reliability and suitability for implementation in a small volume, all of which are critical for a portable artificial heart driver.

However, an additional requirement for such an application is redundancy, which is not readily available from a conventional application of scotch-yoke technology wherein a motor 68 (FIG. 5) with a rotating output shaft is the driving source for actuating the reciprocating pistons of the pump.

The present invention provides an ingenious solution to this problem in a configuration designed particularly to meet the critical redundancy requirements of the SynCardia artificial heart driver.

SUMMARY OF THE INVENTION

The invention lies in the recognition that a conventional scotch yoke may be modified advantageously by creating a gap in the yoke's structure that allows the engagement and disengagement of the yoke from the cam follower that drives it. As a result, two scotch yokes may be combined to provide redundant operation. In particular, because of its simplicity of design and structural compactness, the invention enables redundant operation of a drive for a portable artificial heart.

Accordingly, in the preferred embodiment of the invention a primary scotch yoke and a secondary scotch yoke are coupled in side-by-side arrangement and rigidly attached to a linearly reciprocating element. Each scotch yoke includes a rotary actuator with a cam follower and a yoke attached to the reciprocating element. The yokes have a cam surface incorporating an open gap wherein the follower is disengaged. Under normal operation, the follower of the secondary scotch yoke idles within this gap. A controller is utilized to detect a failure of the primary drive system and, in such event, it disables the primary drive and energizes the secondary drive. Upon activation of the secondary drive system, the secondary follower/yoke pair forces the primary follower into the idling gap of the primary yoke where it remains as the secondary yoke continues to provide uninterrupted motion to the reciprocating element.

Because of these functional features, the scotch-yoke assembly of the invention is most suitable to provide the critical redundancy required to drive a portable artificial heart such as the SynCardia device described above. Additional features and advantages of the invention will be forthcoming from the following detailed description of certain specific embodiments when read in conjunction with the accompanying drawings and claims.

DESCRIPTION OF THE PREFERRED EMBODIMENTS

Figure 1:
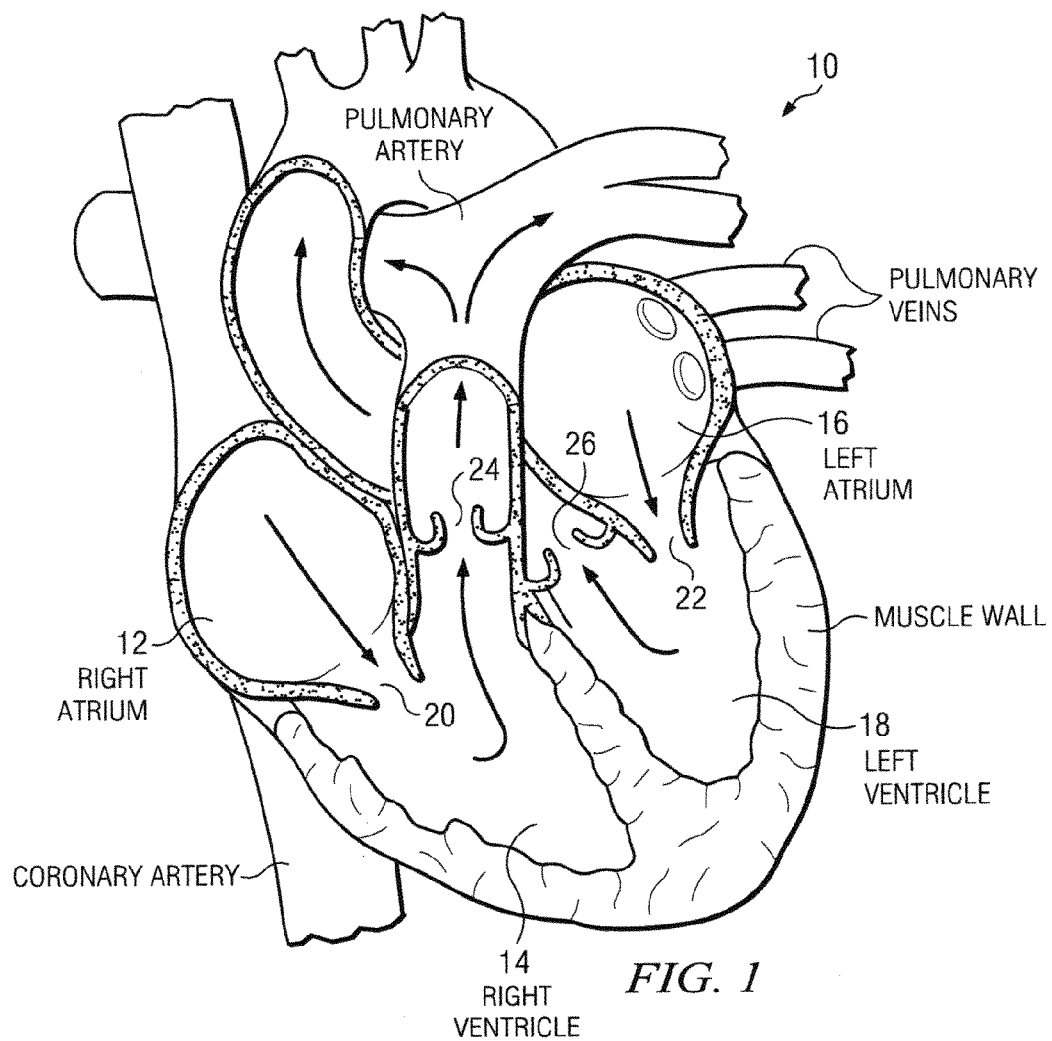
FIG. 1 is a representation of a human heart.
Figure 2:
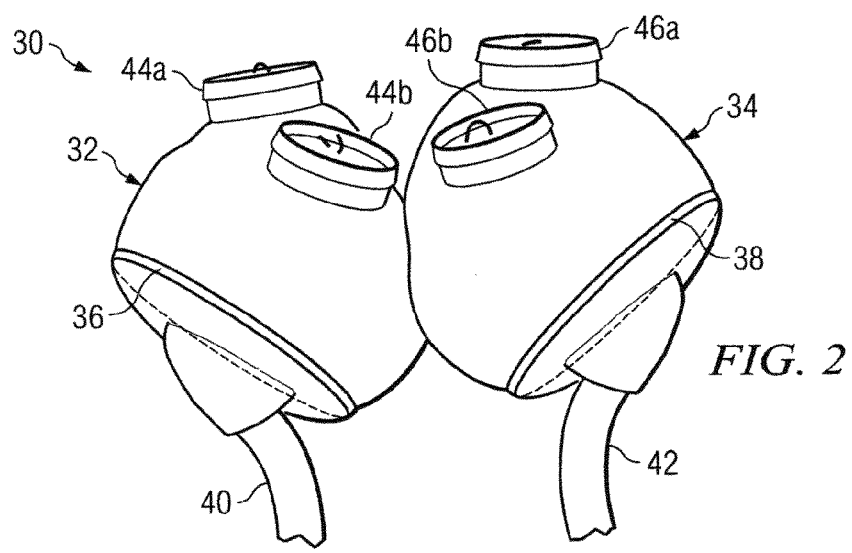
FIG. 2 is a schematic view of the SynCardia artificial heart for which the present invention has been developed.
Figure 3:
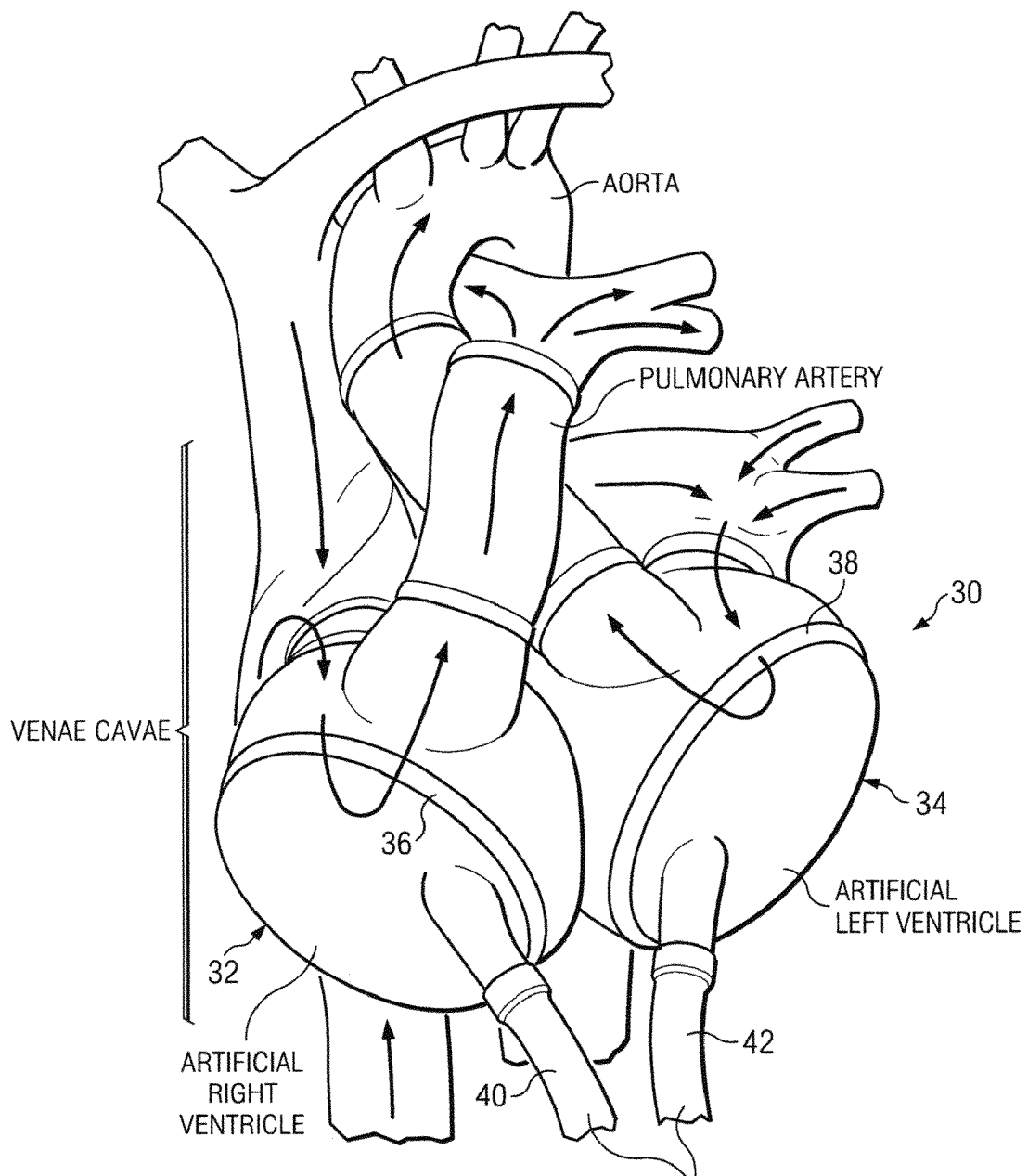
FIG. 3 is a representation of the artificial heart of FIG. 2 connected to the heart atria of a human body.
Figure 4:
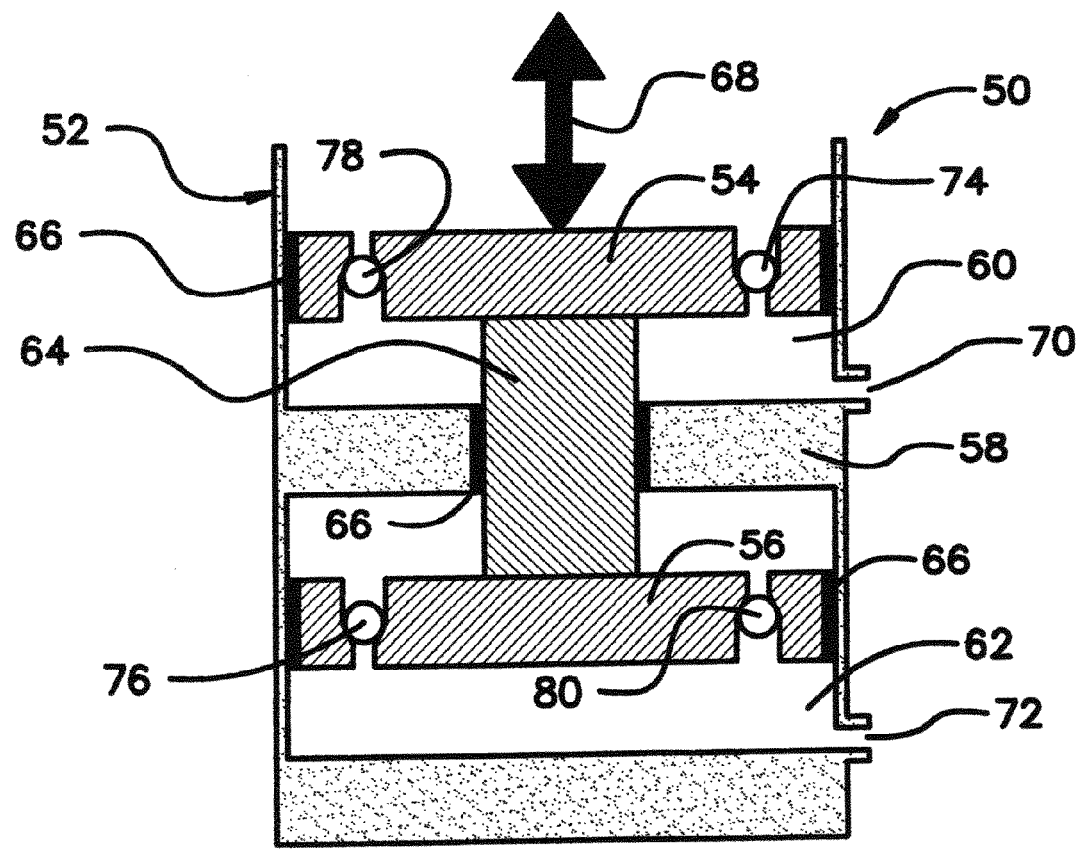
FIG. 4 is a schematic view of a pneumatic driver according to the preferred embodiment of the invention disclosed in Ser. No. 12/454,440.
Figure 14:
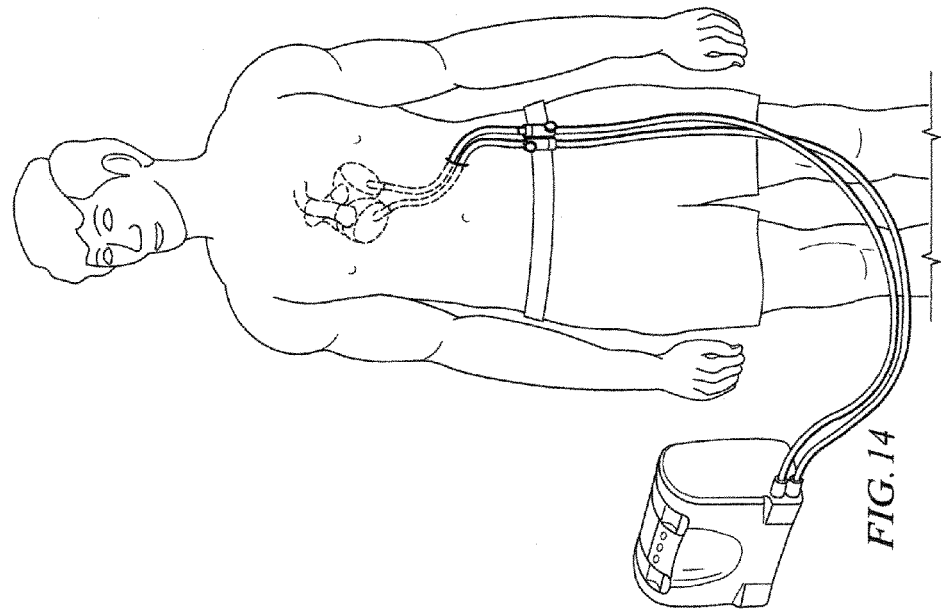
FIG. 14 is an illustration of a portable driver actuated by the scotch-yoke assembly of the invention and connected to an artificial heart implanted in a human body.
Figure 5:
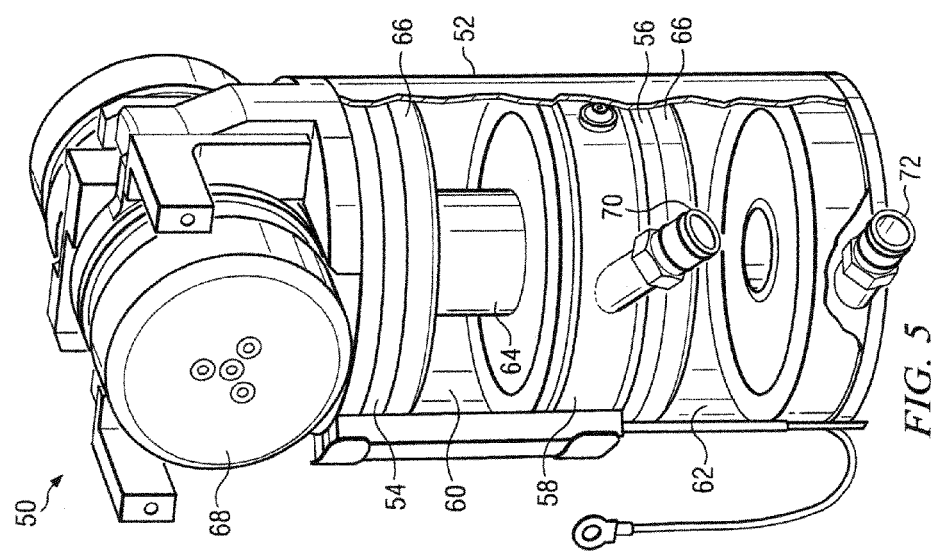
FIG. 5 is a sectioned view of the actual pneumatic driver that incorporates the concepts of the invention disclosed in Ser. No. 12/454,440.
Figure 6:
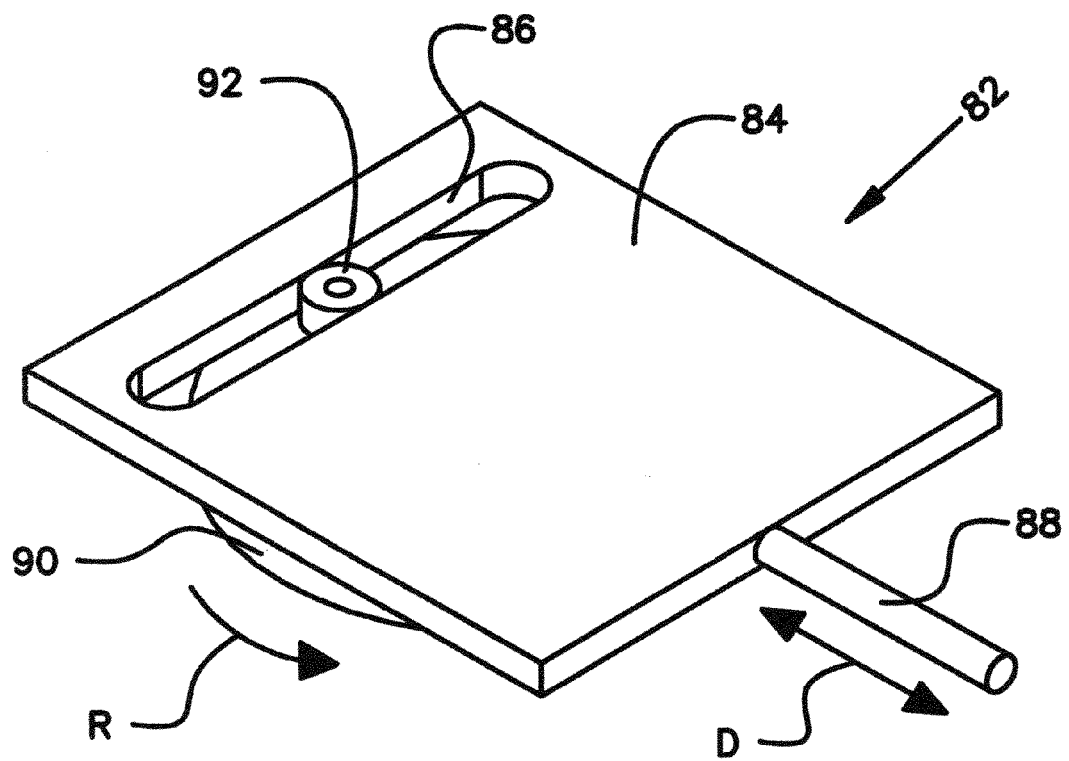
FIG. 6 is a schematic illustration of a conventional scotch yoke.

FIG. 6 is a schematic illustration of a conventional scotch yoke, a device considered to be the most compact rotary-to-linear conversion mechanism (and vice versa). The typical scotch yoke 82 comprises a yoke 84 with a slot defining a cam 86 connected through some rigid means, such as a connecting rod or other element 88, to a target device requiring reciprocating linear translation (not shown). The scotch yoke is constrained so as to cause the rod 88 to follow the linear path meeting the target requirement. A rotary actuator 90 interfaces with the yoke via a cam follower 92. As the rotary actuator rotates, the cam follower pushes the yoke in one direction and then the other in a reciprocating, periodic manner. The motion of the reciprocating element 88 is a pure sine wave over time for a constant rotational speed of the actuator 90.

In some critical applications, such as for a pump driving an artificial heart, it is necessary to provide a backup for the drive system. If the primary drive is determined not to meet some critical operational characteristic, then it will be deactivated and a backup drive will be activated, and the switching must occur without loss of operation. In such a critically redundant system for an artificial heart, it is particularly desirable to use the scotch-yoke mechanism because of its relative simplicity, reliability and suitability for implementation in a small volume.

Still with reference to FIG. 6, it is apparent that only half of the surface of the cam 86 is actively engaged by the cam follower 92 during a cycle of rotation of the rotary actuator 90. That is, if the actuator rotates in the direction indicated by the arrow R in the figure, the left half of the bottom cam surface is engaged while the follower pushes the rod 88 down (toward the right side of the figure), and the right half of the top cam surface is engaged while the follower pushes the rod up) toward the left side of the figure). The balance of the cam surface remains disengaged at all times. Therefore, according to the invention, such unused portions of the cam are removed and the gaps so created are exploited to enable the automatic switching between two scotch yokes coupled to the same reciprocating element in the system. Accordingly, the system provides the type of redundancy critically needed for a portable artificial heart drive, such as the SynCardia device described above.

Figure 7A:
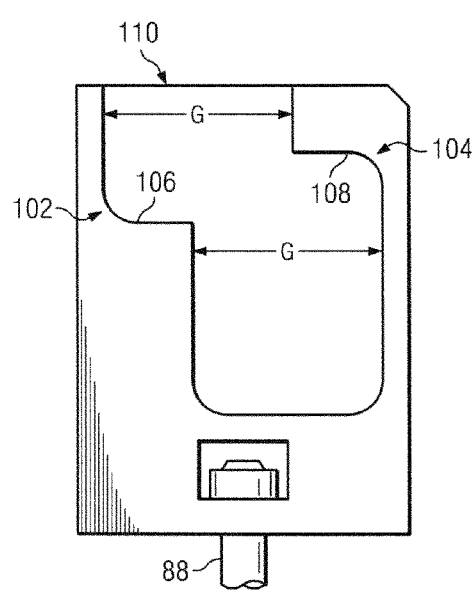
FIGS. 7A-7F show schematically the modified scotch yoke of the invention in several rotational positions to illustrate the sequence of engagement of the yoke cam by the cam follower during a cycle of operation.
Figure 7B:
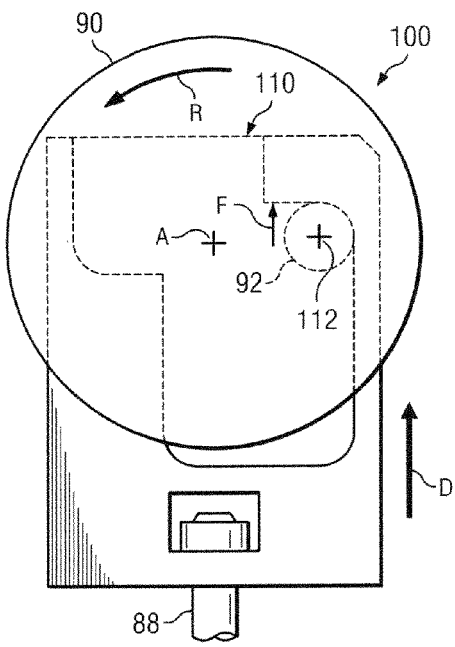

FIGS. 7A-7E illustrate a scotch yoke 100 modified according to the invention. As mentioned, the conventional yoke 84 of FIG. 6 is modified so as to provide two gaps G in the cam, retaining as cam surfaces only most of the active segments required for operation in a predetermined direction. For example, for an actuator rotating 90 counterclockwise with respect to a side viewer, as seen in FIG. 7B, the yoke 100 of the invention would comprise two yoke sections 102 and 104 with respective cams 106 and 108 separated by the gaps G, as illustrated in FIG. 7A with the rotary actuator 90 and the cam follower 92 removed from the cam structure. The cams 106, 108 are preferably formed in a block 110 that is connected to the reciprocating rod 88. As shown in the elevational side view of FIG. 7B, the scotch yoke 100 also includes the rotary actuator 90 that propels it in the usual manner through a follower 92 (shown in phantom line because obscured to a viewer by the actuator 90). Differently from conventional ones, the scotch yoke 100 is capable of operation only with the rotary actuator rotating in a single direction, as illustrated by the arrow R in the figure. However, this apparent drawback is the advance that makes it possible to implement the desired automatic switching between coupled scotch yokes that is required when driving an artificial heart.

FIGS. 7B-7F illustrate the function of a primary scotch yoke 100 driven by a rotary actuator 90 rotating counterclockwise, as indicated by the arrow R. The actuator 90 rotates around a fixed axis A and the cam follower 92 is positioned radially from the axis A so as to follow a circular path as the actuator rotates. The follower 92 is preferably also capable of rotation around its own axis 112 in order to minimize the friction generated by its engagement of the cam surfaces. As a result of the rotation of the actuator 90, the cam follower 92 pushes the yoke in one linear direction or the other, as indicated by the arrows D in the figures, depending on the position of the follower during the cycle of operation of the actuator.

Figure 7C:
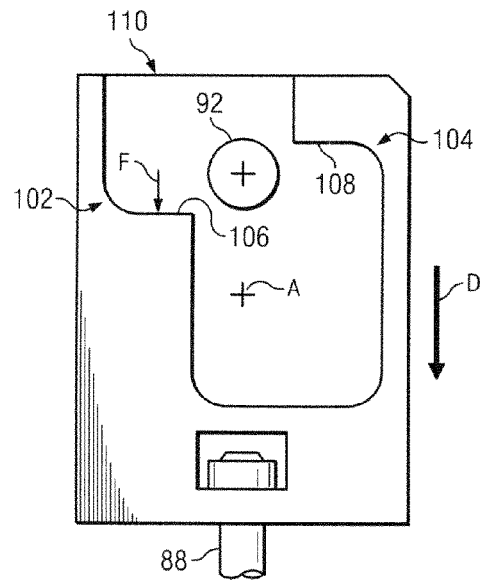
Figure 7D:
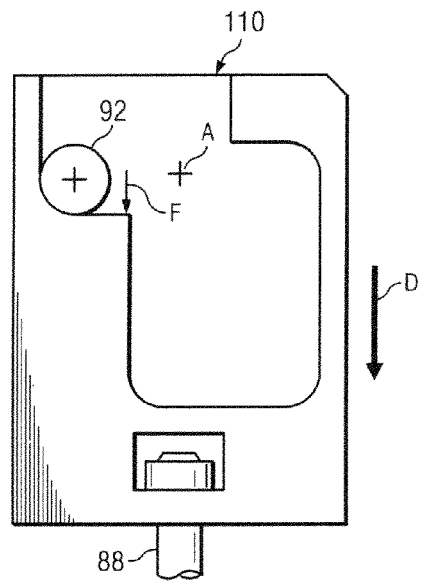
Figure 7E:
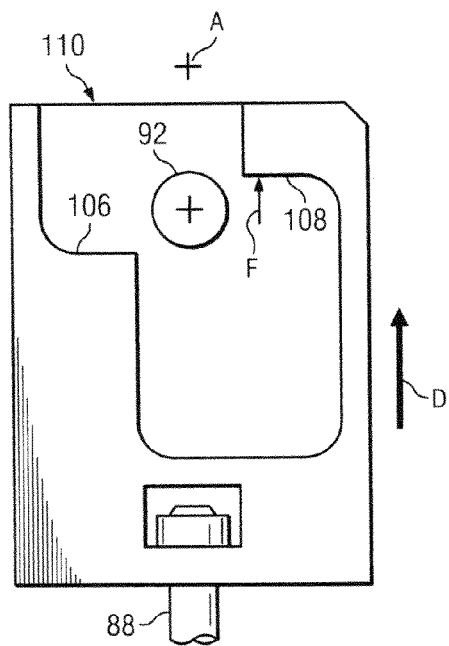
Figure 7F:
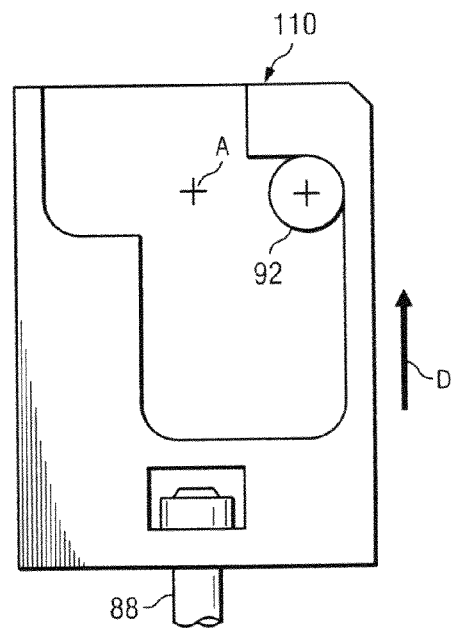

For example, when in the position of FIG. 7B, the follower 92 will push the yoke section 104 upward, in the direction indicated by the arrow F. Therefore, the block 110 and the reciprocating rod 88 attached to it will also move in the upward direction, as indicated by the arrow D. This will continue for 90 degrees of rotation of the cam follower 92, until the follower reaches the top of the circular path defined by the rotation of the actuator 90 around its fixed axis A, as illustrated in FIG. 7C. (Note that the actuator 90 is no longer shown in the remaining figures for clarity of illustration, its presence and relative position being illustrated by the placement of its axis of rotation A.) At the precise top position shown in FIG. 7C, the vertical direction of motion of the follower 92 switches and the force applied on the scotch yoke will similarly switch from the cam 108 of yoke section 104 to the cam 106 of yoke section 102 within a few degrees of rotation of the actuator 90, thereby causing the motion of the yoke, and therefore also of the rod 88, to switch to the opposite (downward) direction, as indicated by arrow D. Note that the follower 92 will disengage the cam 108 and immediately engage the cam 106. Therefore, the action of the follower 92 on the yoke 100 is essentially continuous in spite of the gap G in the cam. The direction of the force applied to the cam and of the motion of the yoke/rod assembly remains downward for the next 180 degrees of rotation of the actuator 90, as illustrated in FIGS. 7D and 7E. When the follower 92 reaches the bottom of its circular path (FIG. 7E), the force applied by the follower 92 on the yoke switches (again within a few degrees or rotation of the actuator 90) from the cam 106 back to the cam 108, thereby causing the motion of the yoke and rod to switch back to the upward direction, as indicated by arrow D, where it remains for the next 180 degrees of rotation. FIG. 7F illustrates, halfway through the upward motion of the yoke 100, the completion of a cycle of rotation of the actuator 90 (the same position shown in FIG. 7B).

Figure 8A:
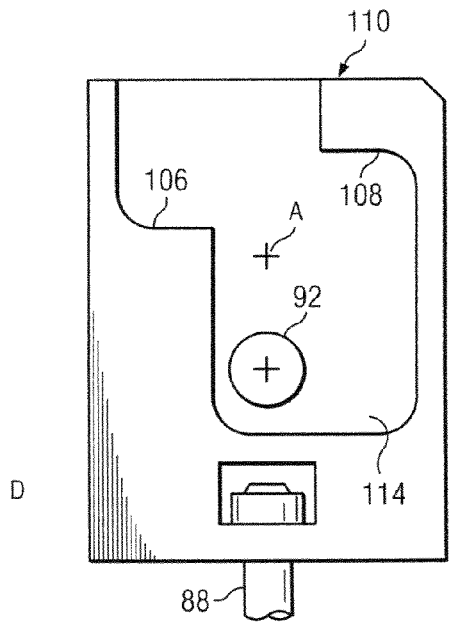
FIGS. 8A and 8B illustrate schematically the disengagement of the yoke from the cam follower afforded by the scotch-yoke configuration of the invention.
Figure 8B:
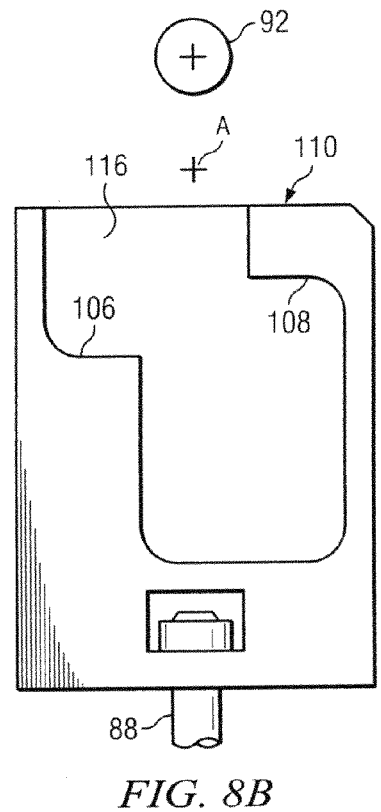

It is apparent that the gap sections G of the scotch yoke of the invention make it possible to disengage the follower 92 from the yoke when the motion of the rotary actuator 90 is interrupted, such as when it fails. For example, should the actuator 90 break down immediately prior to reaching the position illustrated in FIG. 7E, the follower 92 could be disengaged simply by braking the inertial rotary motion of the actuator 90 so as to cause the follower 92 to stop in a position aligned with the bottom gap G between the yoke sections 102,104. As illustrated in FIG. 8A, this would allow the reciprocating motion of the yoke block 110 to continue without obstruction by the idled follower 92. In such a case, assuming the yoke block 100 was driven in the same manner by a separate actuator, it could proceed with its upward motion while the follower 92 remained in its idle position clearing the yoke through the slot 114 defined by the bottom gap G. The same could be achieved at the opposite end of the rotation cycle if the breakdown occurred prior to reaching the position illustrated in FIG. 7C near the top gap G. In such case, as shown in FIG. 8B, the yoke block 100 could continue reciprocating with its downward motion while the idle follower 92 cleared the yoke through the slot 116 defined by the top gap G. Therefore, differently from prior-art embodiments, the scotch yoke of the invention is suitable for use in a system that requires its disengagement, so that the reciprocal motion of the yoke can continue even when its rotary drive fails.

Figure 9:
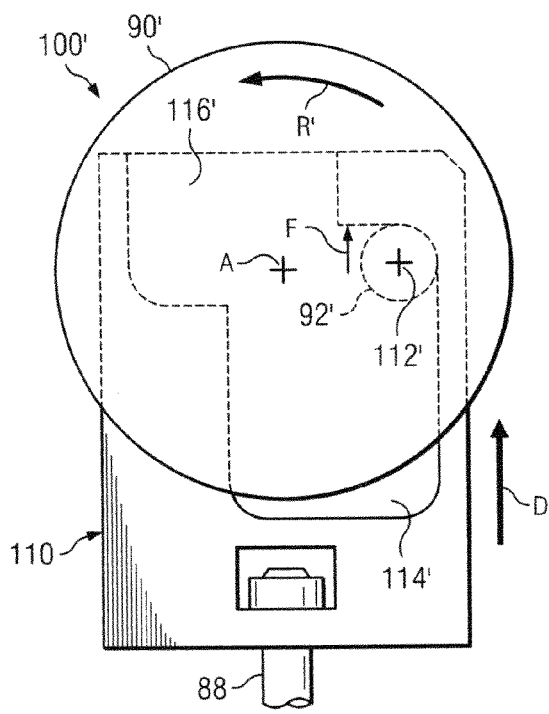
FIG. 9 illustrates the secondary scotch yoke coupled in side-by-side configuration with the primary yoke of FIG. 7 and to a common linearly reciprocating element according to the invention.

A further critical advantage of this feature of the invention lies in the fact that it can be similarly exploited to provide the automatic switching for engagement by a secondary, back-up scotch yoke as required for continued redundant operation of a linearly reciprocating drive. Thus, according to the invention, a secondary scotch yoke 100' configured exactly the same way as the primary scotch yoke 100 shown in FIGS. 7A-7F, but coupled side-by-side in opposing fashion to the primary scotch yoke, is coupled to the same rod 88 (or other reciprocating element requiring redundancy of operation with automatic switching between two independent actuating mechanisms). Preferably, the cams of both yokes are formed in a single block 110 with the same exact geometry; that is, such that a 90-degree rotation of the block 110 would show exactly the same cam configuration (that of FIG. 7A). FIG. 9 illustrates such secondary, alternatively engaged, scotch yoke 100' in the same position as the primary yoke 100 of FIG. 7B. A secondary cam follower 92' is rotatably coupled to a secondary actuator 90' for engagement of the cams 106' and 108' of the secondary yoke during the cycle of operation of the actuator 90'. The secondary rotary actuator 90' is aligned with the primary actuator 90 along the common axis of rotation A and it is similarly able to rotate only in one direction R', counterclockwise. However, while still counterclockwise with respect to a side viewer, as shown in the figure, the direction R' in fact is opposite to the direction R of the primary actuator with reference to the common axis of rotation A. That is, if the direction of rotation R of the primary actuator is counterclockwise relative to the axis A, the direction of rotation R' of the secondary actuator is clockwise relative to the same axis A viewed from the same vantage point. Thus, it is clear that in absolute spatial terms the actuators rotate in opposite directions.

Figure 10B:
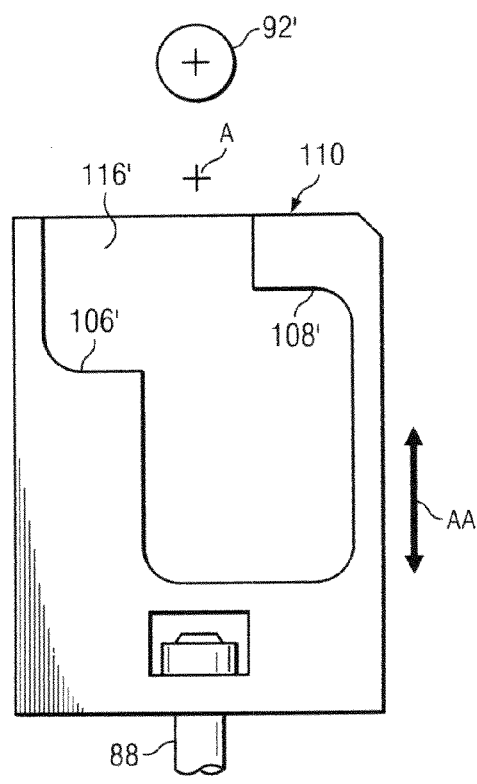
FIGS. 10A and 10B illustrate schematically, using the scotch yoke of FIG. 9 as example, the required idle positions of the cam follower in order to effect its engagement of, or disengagement from, the yoke of the invention without interference with the continued linear motion of the yoke.
Figure 10A:
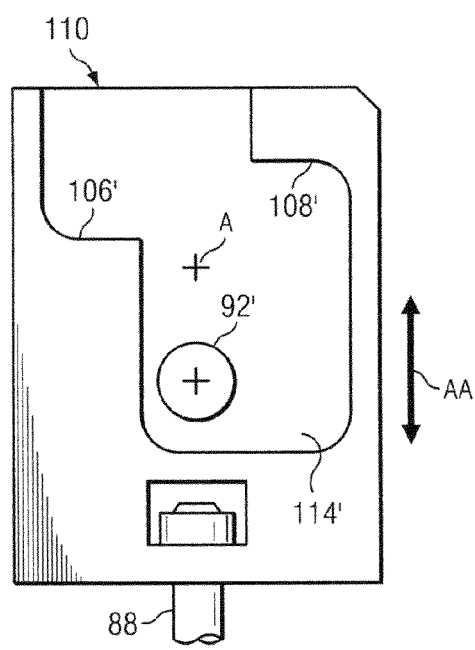

In practice only one of the scotch yokes is energized at any given time and the system is configured so that the secondary yoke is automatically engaged when the primary yoke fails and becomes disengaged (or vice versa). Each actuator 90,90' is engineered to stop only at positions wherein the cam followers 92,92' are aligned with the gaps (114,116 and 114', 116', respectively), so that the block 110 incorporating both yokes can continue its linear movement in both directions, propelled by the functioning cam follower, without interference from the idle follower. This condition is achieved if the cam follower stops immediately upon entering the gap encountered after the failure of the rotary actuator, which can be accomplished by friction and/or a braking mechanism. Thus, for example, in its idle condition the secondary cam follower 92' would be positioned either in alignment with the gap 114' as shown in FIG. 10A, or with gap 116' as shown in FIG. 10B, and the yoke block 110 could continue to move freely in its reciprocating linear motion (indicated by arrow AA). Similarly, in its idle condition the primary cam follower 92 would be positioned either in alignment with the gap 114 or the gap 116 as shown in FIGS. 8A and B, respectively.

Note that, because of the configuration of each cam, the secondary drive system will drive the primary follower to the idle gap automatically when the primary actuator fails and the secondary one is energized. The only requirement is that the primary system have sufficient friction or electronic brake to keep it from over-rotating when it reaches the gap. That is, it is not necessary for the primary follower to stop in a gap. The primary system can fail anywhere and, as soon as the secondary system begins driving the reciprocating element, it also drives the primary yoke that in turn drives the primary follower to the primary idle gap. Once the primary follower reaches its idle gap, it will no longer contact the yoke and the secondary will no longer need to drive it. It is clear that the functions of the primary and secondary systems, as described, are interchangeable.

Assuming a failure of the primary actuator 90 while operating in the quadrant of FIG. 7B according to the cycle illustrated in FIGS. 7B-7F, the actuator would stop in the position of FIG. 7C. The immediate subsequent actuation of the secondary rotary actuator 90' would cause the secondary cam follower 92' to bear on its cam 106' and continue the reciprocating motion of the rod 88 through the action of the yoke sections 102' and 104'. If, for example, the secondary cam follower 92' had been idle in the position shown in FIG. 10A, it would be able to rotate unhindered through the gap 114' to engage the cam 106' and push the yoke down (as illustrated by arrow F in FIG. 7D with reference to the primary yoke). If, on the other hand, the secondary cam follower 92' had been idle in the position shown in FIG. 10B, it would immediately engage the cam 106'. The follower 92' would similarly engage the cam 108' and push the yoke upward if the primary rotary actuator failed with its follower v92 in the down position of its circular motion.

Thus, by coupling the reciprocating element 88 to both primary and secondary scotch yokes as shown herein, the continuity of its motion is assured by the ability to automatically switch from the primary to the secondary actuator in case of failure. The two scotch yokes are preferably combined facing one another, as taught, coupled to the reciprocating element 88 to provide the exact same linearly reciprocating motion. Sensors and controllers are utilized in conventional manner to detect at all times the motion of the yokes and, upon failure of the primary rotary actuator, to stop its rotation and at the same time energize the secondary actuator. The stopped position of the idled cam follower is controlled with friction or a conventional braking mechanism.

Figure 11:
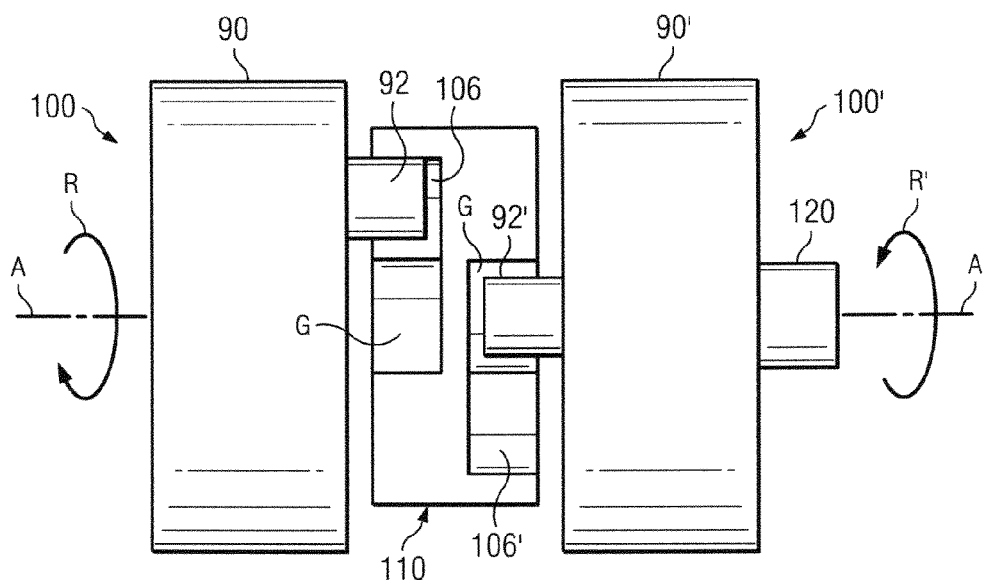
FIG. 11 is a schematic top view of the scotch-yoke assembly of the invention.
Figure 12:
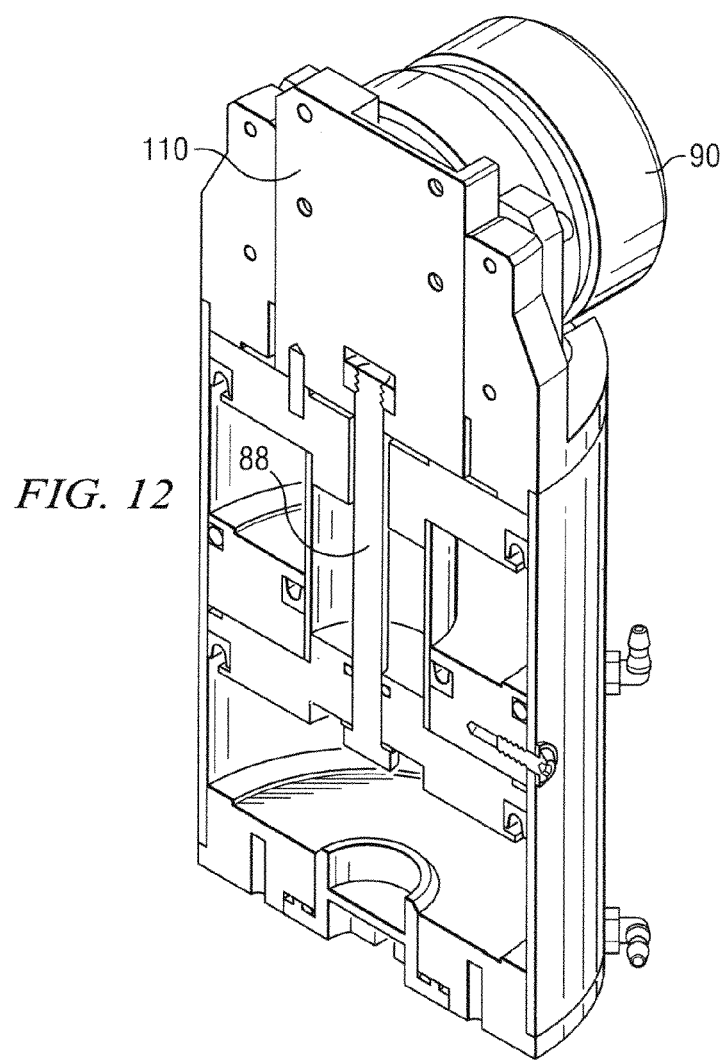
FIG. 12 is a sectioned view of an actual scotch-yoke assembly that incorporates the concepts of the invention.
Figure 13:
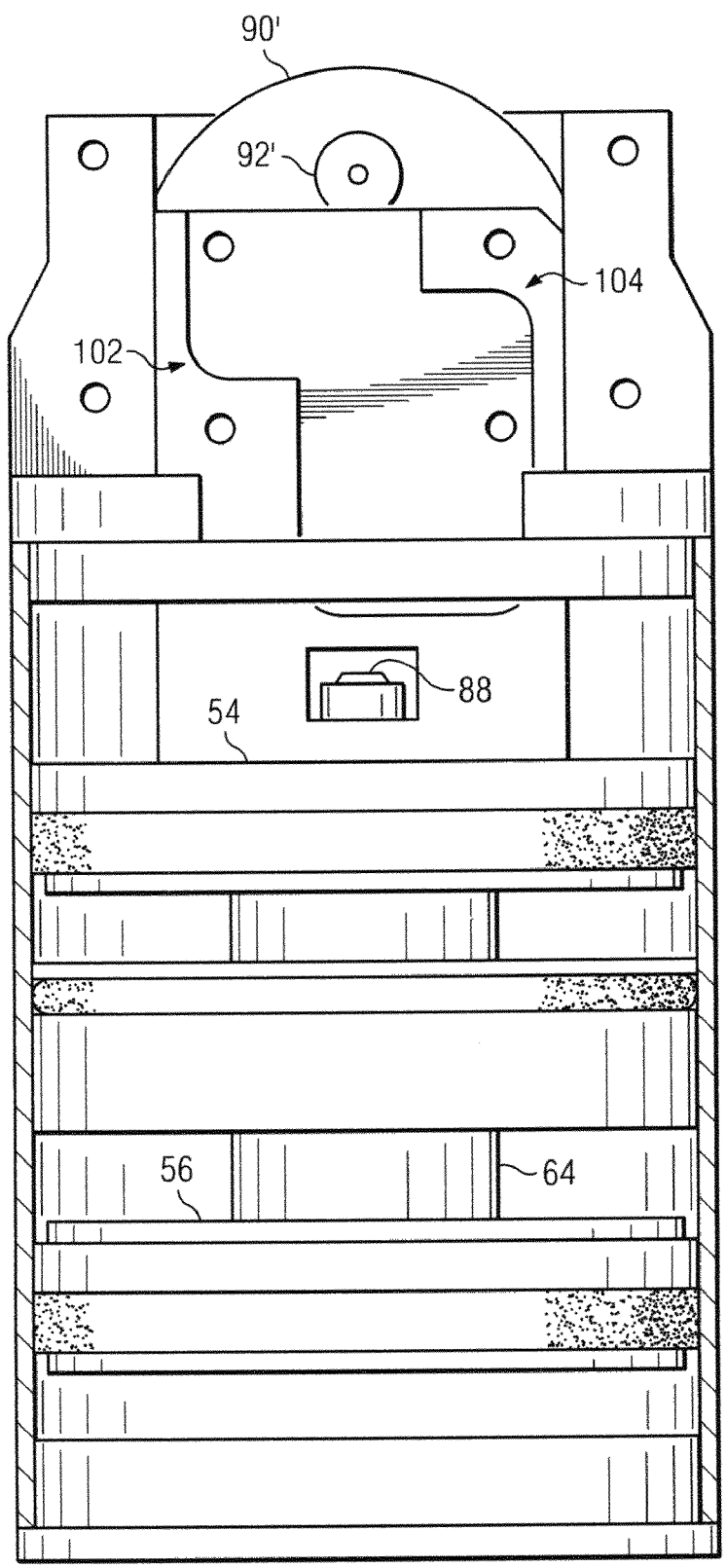
FIG. 13 is another sectioned view of the assembly showing the cam of the primary yoke and the idle follower of the secondary yoke

FIG. 11 is a schematic top view of a scotch-yoke assembly according to the invention to illustrate the side-by-side opposing arrangement of the scotch yokes described in FIGS. 7 and 9. The primary scotch yoke 100 is shown on the left-hand side of the figure with the cam follower 92 driving the cam surface 106 during rotation of the primary rotary actuator 90. The block 110 incorporating both yoke sections is attached to the linearly reciprocating element 88 (not shown in this top view). The secondary scotch yoke 100' is coupled to the primary one by having its cam incorporated into the same block 110 opposite to the cam of the primary yoke. The secondary rotary actuator 90' is shown idle at the top of its rotation cycle with its cam follower 92' positioned in the gap G of the secondary yoke. A controller 120 is provided to detect a failure in the primary scotch yoke 100 (such as, for example, a break down in the actuator 90, or a failure in the follower's bearing); in such event, to de-energize the primary actuator and stop its motion so that the cam follower becomes idle at a position in the gap G that will not interfere with the continued reciprocating motion of the yoke block 110; and then to energize the secondary rotary actuator 100' so as to cause its cam follower 92' to immediately engage the cam section 106' and continue operating the assembly. FIG. 12 is a sectioned view of an actual scotch-yoke assembly that incorporates the concepts of the invention. FIG. 13 is another sectioned view of the assembly showing the cam of the primary yoke and the idle follower of the secondary yoke. Finally, FIG. 13 is an illustration of a portable driver actuated by the scotch-yoke assembly of the invention and connected to an artificial heart implanted in a human body.

While the invention has been shown and described herein with reference to what is believed to be the most practical embodiment, it is recognized that departures can be made within the scope of the invention. For example, the two scotch yokes have been illustrated in opposing side-by-side configuration, but they could be arranged in any other manner allowing the disengagement of the primary one upon its failure and the subsequent engagement of the secondary one. For example, a mirror-image configuration would work with both actuators rotating in the same spatial direction. In fact, the two yokes could be coupled to the reciprocating element in any arbitrary manner, so long as they were both configured to produce the same reciprocating motion and to enable the deactivation/activation procedure described herein. Therefore, the invention is not to be limited to the disclosed details, but is intended to embrace all equivalent structures and methods.

I claim:

1. A scotch-yoke assembly comprising:
a primary scotch yoke and a secondary scotch yoke rigidly attached to a linearly reciprocating element, each of said scotch yokes including a rotary actuator with a cam follower and a yoke attached to the reciprocating element, each said yoke having a cam with an open gap through which the follower may be stopped and disengaged from the cam;
a controller adapted to detect a failure in the primary scotch yoke, disengage said cam follower of the primary scotch yoke from the cam of the primary scotch yoke, and energize the secondary scotch yoke.

2. The scotch-yoke assembly of claim 1, wherein said primary scotch yoke and said secondary scotch yoke are coupled in an opposing arrangement.

3. The scotch-yoke assembly of claim 1, wherein said reciprocating element is an actuator for a pneumatic pump.

4. The scotch-yoke assembly of claim 3, wherein said primary scotch yoke and said secondary scotch yoke are coupled in an opposing arrangement.

5. The scotch-yoke assembly of claim 3, further comprising an artificial heart connected to said pneumatic pump.

6. The scotch-yoke assembly of claim 5, wherein said primary scotch yoke and said secondary scotch yoke are coupled in an opposing arrangement.

* * * * *

UNITED STATES PATENT AND TRADEMARK OFFICE
CERTIFICATE OF CORRECTION

PATENT NO. : 8,070,455 B2
APPLICATION NO. : 12/498991
DATED : December 6, 2011
INVENTOR(S) : Frank A. Tinker It is certified that error appears in the above-identified patent and that said Letters Patent is hereby corrected as shown below:

In the title page, item (73), please replace the Assignee from "Syngardia Systems, Inc." to --SynCardia Systems, Inc.--.

Signed and Sealed this
Nineteenth Day of March, 2013

Teresa Stanek Rea
*Acting Director of the United States Patent and Trademark Office*